United States Patent [19]
Bohn

[11] Patent Number: 5,637,450
[45] Date of Patent: Jun. 10, 1997

[54] DECONTAMINATED SERUM AND METHOD OF PRODUCTION THEREFOR

[76] Inventor: Burghard Bohn, Karlsruher Strasse 6, 6900 Heidelberg, Germany

[21] Appl. No.: 301,041

[22] Filed: Sep. 7, 1994

Related U.S. Application Data

[63] Continuation of Ser. No. 938,264, filed as PCT/DE91/00307, Apr. 13, 1991, published as WO91/16082, Oct. 31, 1991, abandoned.

[30] Foreign Application Priority Data

Apr. 18, 1990 [DE] Germany ............ 40 12 323.5
May 9, 1990 [DE] Germany ............ 40 14 063.6

[51] Int. Cl.$^6$ ............ A01N 1/02; C12Q 1/32
[52] U.S. Cl. ............ 435/2; 435/26
[58] Field of Search ............ 435/2, 240.3, 240.31, 435/26; 424/531

[56] References Cited

U.S. PATENT DOCUMENTS

| | | | |
|---|---|---|---|
| 4,473,647 | 9/1984 | Carpenter | 435/240 |
| 4,533,634 | 8/1985 | Maldonado | 435/240 |

FOREIGN PATENT DOCUMENTS

| | | | |
|---|---|---|---|
| 62-035259A | 2/1987 | Japan. | |
| 1471336 | 4/1977 | United Kingdom. | |

*Primary Examiner*—Ralph Gitomer
*Attorney, Agent, or Firm*—Staas & Halsey

[57] ABSTRACT

Decontaminated biological material, particularly liquids, and a method for decontaminating biological material, wherein serum is employed in cell structures for cultivating human and animal cells and used during the preparation of proteins and similar pharmaceutical products which are prepared by using cell culture of fused cells, originated from humans or animals and the like.

15 Claims, No Drawings

DECONTAMINATED SERUM AND METHOD OF PRODUCTION THEREFOR

This application is a continuation of U.S. patent application Ser. No. 07/938,264, filed as PCT/DE91/00307, Apr. 13, 1991 published as WO91/16082, Oct. 31, 1991, now abandoned.

BACKGROUND OF THE INVENTION

1. Field of the Invention

The invention concerns decontaminated biological material, especially liquids, and a method for decontaminating biological material, especially biological liquids.

2. Description of the Related Art

In numerous fields of research and development as well as in industrial and professional fields serum, especially calf serum and fetal calf serum, is used. This serum is employed in cell cultures for cultivating human and animal cells. Furthermore it is used during the preparation of proteins and similar pharmaceutical products, which are prepared by means of cell cultures of fused cells originated from humans or animals, some cases originated from insects also.

The term biological material or biological liquid, respectively, means material or liquid, respectively, derived from biological origin.

The quality of such serum depends on its ingredients; for example, insulin and transferrin are of special importance.

Serum, especially calf serum and fetal calf serum, is sensitive to heat especially concerning important biological components.

In consequence it is not possible, for example, to obtain a decontamination of these biological materials by increasing temperature or by making the serum hot, respectively.

Such decontamination is necessary especially for inactivating viruses, as for instance foot and mouth virus, retroviruses, for instance HIV virus or related viruses, as well as other susceptible infectious agents.

For inactivation it does not suffice for instance to perform a so called "pasteurization" at 60° C. Also it is not possible, to perform a biological decontamination in a satisfactory manner by heating over this pasteurizing temperature, for example by heating at 65° C. for two times half an hour. These denaturing condition cause changes of biological activity, based for instance on a depolymerization of aggregates and a denaturing of proteins.

Concerning the methods in the prior art it is worthwhile to mention in particular the biological decontamination by X-ray radiation, especially the inactivation of viruses. In this connection, see the reference "Canadian Journal of comparative Medicine", 45:397–399 (1981).

The radiation of biological material for destruction of viruses with the required high doses is injurious to the quality of the biological material.

Also the chemical agents, employed for biological decontamination especially for inactivation of viruses for instance Ethylenoxid, cause in some cases an insufficient decontamination on the one hand and on the other hand a prejudice of the biological material.

"A prejudice of the biological material" means, for instance, a prejudice (adverse effect on) the promotion of cell growth, which prejudice occurs by reason of the above described methods of altering components.

Consequently, the methods in the prior art for biological decontamination of biological material, especially biological liquids, have the disadvantages of insufficient efficiency and/or of prejudices of the quality of the biological material or its components, respectively.

SUMMARY OF THE INVENTION

Therefore it is an object of the present invention to provide a method for biological decontamination and to provide decontaminated biological material, whereby the biological decontamination, especially the inactivation of viruses, is obtained in an effective and preserved manner.

Concerning decontaminated biological material, especially liquids, in accordance to the invention this object is solved in that it is decontaminated by treatment with acid following by treatment with alkali. This way of solution is specified, as well as numerous preferred embodiments of this way of solution.

It turns out that the inactivation of viruses, for instance of acid-sensitive retroviruses is quickly forced up.

Thereby, as shown by cell culture cultivation experiments, the biological components of the serum will not be prejudiced.

Consequently, a serum according to the invention or treated according to the invention, respectively, has a quickly increased efficiency regarding the use in research and industry.

In particular it is a positive feature of the present invention that the ionic strength of the serum according to the invention or treated according to the invention, respectively, only changes insignificantly and in consequence only small changes of osmolarity appear, for instance in the range of 20 to 30 m Osmol.

In the method according to the invention or the product according to the invention respectively, the buffer capacity is relative quickly broken through and a lowering of the pH value is obtained, whereby with the parameters according to the invention for instance the inactivation of of viruses and in general the biological decontamination is obtained.

DETAILED DESCRIPTION OF THE PREFERRED EMBODIMENTS

The invention concerns lowering the pH value with acid, especially mineral acids of low normality, for instance with 1N hydrochloric acid, maintaining the therewith treated material at low pH value for a period of 3 hours, for instance, and then increasing the pH value. An especially favorable pH value is the pH value of 4.9.

The temperature is maintained in the range of 0° C. and 60° C., and more preferably in the range of the temperature of a refrigerator, about +4° C., and room temperature; (25° C.) therefore the heat sensitive biological components of the serum remain intact; also the biological components which are heat sensitive at lowered pH value remain intact.

With the method according to the invention or the product according to the invention, all viruses as well as retroviruses are effectively inactivatable or inactivated, respectively.

For increasing the pHs to a desirable value, in particular a physiological value of about 7 to 7.5, an alkali of low normality, especially 1N soda lye is used.

For lowering the pH's other suitable acids with appropriate dissociation constants may be used.

Also other alkali as for instance potash lye or organic alkali may be employed to increase to pH.

The selection of the suitable alkali or acid respectively, depends on the proposed employment of the serum with regard to cell culture, composition of the media, ionic content and the like.

By reason of the common expert knowledge of one of skill in the art, a suitable selection in each individual case is possible without more ado.

By the method according to the invention it is also possible to employ serum or fetal calf serum, respectively, derived from regions with a high potential biological load of contamination, in cell culture as well as in the fields of industry and pharmaceuticals and for research.

In the following an embodiment of the invention is pointed out.

One liter of fetal calf serum is lowered to a pH value of 4.9 with sterile one normal HCl and maintained at this value for two hours at +4° C. (cooler).

Subsequently the pH is increased up to a value of pH 7.3 by the addition of sterile 1N NaOH.

The material obtained in that way is used for cultivation of adherent cells.

Thereby 1×10 cells were seeded in a cell culture dish with 20 ml liquid culture volume and 10% serum content.

The number of cells obtained is 3.2×10 after 2 days, 2.3×10 after 5 days and 4.8×10 after 7 days.

The cells show a healthy appearance; cytopathic or virus-specific effects are not observed.

Performed experiments or tests respectively for the presence or absence of inactivation, respectively, were performed with foot and mouth virus and retroviruse and show complete inactivation or removal of viruses.

In many cases during special applications it is desirable to observe the time slope of the efficiency of the acid/alkali treatment, for instance to select the treatment period which is as short as possible. Besides that, an urgency exists to examine a material to determine whether it has been successfully treated according to the invention, this is valid, in particular, when a law requires such examination, as in decontamination for infectious diseases.

It is a further object of the present invention to provide a characteristic or a measuring method, respectively, which allows monitoring or verification of a decontaminating treatment. For decontaminated biological material this object is solved in accordance with the above mentioned designation, in that the status of the treatment and/or the end of the treatment is monitored or determined respectively by determining the (residual) LDH (Lactate-Dehydrogenase) activity.

Furthermore a method is claimed for decontamination of biological material, in particular biological liquids, in accordance with the above mentioned designation, which is characterized in that the progress of the treatment and/or the end point of the treatment is monitored or determined respectively by determining the (residual) LDH (Lactate-Dehydrogenase) activity.

Furthermore the present invention also concerns a method for verifying the status of treatment or the performance of a treatment respectively, by using a key enzyme. The LDH (Lactate-Dehydrogenase) is an enzyme, which is ubiquitously present in calf serum and bovine serum and is existent for instance in calf serum in a concentration of about 100 units/liter and in bovine serum in a concentratiion of about 100 to 500 unit/liter. For the desired efficiency of sera, in particular for cell cultivation and cell growth, LDH is of no account.

Consequently its decay is not relevant to the quality of the serum or the sera respectively. On the contrary, since potential side effects of LDH enzymatic activity are reduced, the biological material or the method, respectively, according to the invention, provide an improvement of quality of the sera or the biological material, respectively.

Additionally in some cases a decay of pyrogens occurs surprisingly, providing a further advantage of the present invention.

In practice it is recommendable to determine the decay of LDH activity either within the scope of measurement of LDH activity before and after a treatment or within the scope of measurement of biological materials and reserve samples associated therewith. Furthermore it is recommended to determine a specific limit or a limiting value, respectively, for actual biological materials as measuring limit or limiting value, respectively, for instance of less than or equal to 40 unit/liter for calf serum. The LDH activity after acid/alkali treatment should decrease by a factor of 4 to 15 and preferably 8 to 12 from the value before acid/alkali treatment.

Embodiments of the present invention are following:

EXAMPLE 1

Fetal calf serum, treated three hours at 4° C. and at a pH value of 4.9 (followed by subsequent increasing up of the pH value) was evaluated concerning LDH activity before and after the treatment. The LDH activity was to 100 unit/liter before the treatment and 8.3 unit/liter after the treatment.

Simultaneously the content of pyrogen lowered from 1.2 ng/ml before to 0.3 ng/ml after the treatment.

EXAMPLE 2

Bovine serum was treated analogous to example 1 and the content of LDH was evaluated before and after the treatment, respectively. The value was 350 unit/liter before and 25 unit/liter after the treatment.

EXAMPLE 3

Bovine serum was treated according to example 1. Before treatment the LDH value was 300 unit/liter and after treatment was 16.6 unit/liter.

I claim:

1. Decontaminated blood products produced by the process comprising the following steps:
  (a) treating blood products potentially having active viruses and having native Lactate-Dehydrogenase activity with acid for 2.5 to 4.0 hours to lower pH to a value of between 3.5 and 5.5 and inactivate viruses in the blood products;
  (b) after step (a), treating the blood products with alkali to increase pH to a value of between 7.0 and 7.5; and
  (c) monitoring at least one of the progress of the process and an end of the process by determining Lactate-Dehydrogenase activity before and after step (a) and comparing the Lactate-Dehydrogenase activity determined after step (a) with the Lactate-Dehydrogenase activity determined before step (a).

2. Decontaminated blood products according to claim 1, wherein the end of the process is monitored by determining when Lactate-Dehydrogenase activity decreases by a factor of 4.0 to 15.0.

3. Decontaminated blood products according to claim 2, wherein the end of the process is monitored by determining when Lactate-Dehydrogenase activity decreases by a factor of 8.0 to 12.0.

4. A method for decontaminating blood products potentially having active viruses and having native Lactate-Dehydrogenase activity, comprising the following steps:

(a) inactivating viruses in the blood products by adding acid to the blood products to decrease pH of the blood products to a value of between 3.5 and 5.5;

(b) after step (a), allowing a predetermined amount of time to elapse:

(c) after step (b), adding alkali to the blood products to increase pH of the blood products to a physiological level; and (d) monitoring at least one of the progress of the process and an end of the process by determining lactate-Dehydrogenase activity before and after step (a) and comparing the Lactate-Dehydrogenase activity determined after step (a) with the Lactate-Dehydrogenase activity determined before step (a).

5. A method for decontaminating blood products according to claim 4, wherein the acid added in step (a) is a mineral acid or an organic acid.

6. A method for decontaminating blood products according to claim 5, wherein the acid added in step (a) is hydrochloric acid.

7. A method for decontaminating blood products according to claim 4, wherein between 2.0 and 5.0 hours is allowed to elapse in step (b).

8. A method of decontaminating blood products according to claim 4, wherein between 2.5 and 4.0 hours is allowed to elapse in step (b).

9. A method of decontaminating blood products according to claim 4, wherein approximately 3.0 hours is allowed to elapse in step (b).

10. A method of decontaminating blood products according to claim 4, wherein the pH is increased to between 7.0 and 7.5 in step (c).

11. A method of decontaminating blood products according to claim 4, wherein steps (a) through (c) are performed at a temperature of between 0° C. and 60° C.

12. A method of decontaminating blood products according to claim 4, wherein steps (a) through (c) are performed at a temperature of between +4.0° C. and +25.0° C.

13. A method of decontaminating blood products according to claim 4, wherein the end of the process is monitored by determining when the Lactate-Dehydrogenase activity decreases by a factor of between 4.0 and 15.0.

14. A method of decontaminating blood products according to claim 4, wherein the end of the process is monitored by determining when the Lactate-Dehydrogenase activity decreases by a factor of between 8.0 and 12.0.

15. A method for decontaminating blood products potentially having active viruses and having native Lactate-Dehydrogenase activity, comprising the following steps:

(a) inactivating viruses in the blood products by adding acid to the blood products to decrease pH of the blood products to a value of between 3.5 and 5.5;

(b) after step (a), allowing between 2.5 and 4.0 hours to elapse;

(c) after step (b), adding alkali to the blood products to increase pH of the blood products to a value between 7.0 to 7.5; and (d) monitoring at least one of the progress of the process and an end of the process by determining Lactate Dehydrogenase activity before and after step (a) and comparing the Lactate-Dehydrogenase activity determined after step (a) with the Lactate-Dehydrogenase activity determined before step (a).

* * * * *